US009916076B2

(12) United States Patent
Okumura et al.

(10) Patent No.: US 9,916,076 B2
(45) Date of Patent: Mar. 13, 2018

(54) ENDOSCOPIC IMAGE DISPLAY DEVICE (71) Applicant: OLYMPUS CORPORATION, Tokyo (JP)

(72) Inventors: Keiji Okumura, Tokyo (JP); Koichi Hirose, Tokyo (JP); Toshiya Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/077,962

(22) Filed: Mar. 23, 2016

(65) Prior Publication Data

US 2016/0202895 A1  Jul. 14, 2016

Related U.S. Application Data (63) Continuation of application No. PCT/JP2014/074426, filed on Sep. 16, 2014.

(30) Foreign Application Priority Data

Nov. 21, 2013  (JP) .................................. 2013-240726

(51) Int. Cl.
 G09G 5/00  (2006.01)
 G06F 3/0485  (2013.01)
 (Continued)

(52) U.S. Cl.
 CPC ........ G06F 3/04855 (2013.01); A61B 1/0005 (2013.01); A61B 1/00045 (2013.01);
 (Continued)

(58) Field of Classification Search
 None
 See application file for complete search history.

(56) References Cited

U.S. PATENT DOCUMENTS

2009/0080744 A1* 3/2009 Sagawa ................. G06F 19/321
 382/131
2009/0131746 A1  5/2009 Seo et al.
 (Continued)

FOREIGN PATENT DOCUMENTS

JP  H11-317930 A  11/1999
JP  2003-052623 A  2/2003
 (Continued)

OTHER PUBLICATIONS

International Search Report and Written Opinion dated Dec. 2, 2014 issued in PCT/JP2014/074426.
 (Continued)

*Primary Examiner* — Jennifer Mehmood
*Assistant Examiner* — Stephen T Reed
(74) *Attorney, Agent, or Firm* — Scully, Scott, Murphy & Presser, PC (57) ABSTRACT

A display control unit (23) scrollably displays a plurality of images to be displayed in a specific display area within a screen. An operation receiving unit (21) receives a scroll instruction and a display mode switching instruction that are issued in response to a user operation. When a display mode is switched, the display control unit (23) switches a display in the display area such that, among the plurality of images in the display area displayed in the first display mode, at least one image located as a position that goes out of the display area first upon scroll in a forward direction is arranged, upon a switch to a second display mode, at a position that also goes out of the display area first upon scroll in the forward direction in the display area.

11 Claims, 8 Drawing Sheets

(51) Int. Cl.
*A61B 1/00* (2006.01)
*G06F 3/0487* (2013.01)
*G09G 5/395* (2006.01)
*A61B 5/00* (2006.01)

(52) U.S. Cl.
CPC .......... *A61B 5/7445* (2013.01); *G06F 3/0485* (2013.01); *G06F 3/0487* (2013.01); *G09G 5/395* (2013.01); *A61B 5/4233* (2013.01); *A61B 5/4238* (2013.01); *A61B 2576/00* (2013.01); *G09G 2340/14* (2013.01); *G09G 2354/00* (2013.01); *G09G 2380/08* (2013.01)

(56) References Cited

U.S. PATENT DOCUMENTS

| | | | | |
|---|---|---|---|---|
| 2009/0225102 | A1* | 9/2009 | Okubo | G06F 17/30265 345/661 |
| 2010/0086286 | A1* | 4/2010 | Lee | A61B 1/0005 386/201 |
| 2011/0032259 | A1* | 2/2011 | Kim | A61B 1/041 345/428 |
| 2011/0105879 | A1* | 5/2011 | Masumoto | G06F 19/321 600/407 |
| 2012/0198384 | A1 | 8/2012 | Kumamoto | |
| 2013/0109915 | A1* | 5/2013 | Krupnik | G06T 3/4038 600/109 |

FOREIGN PATENT DOCUMENTS

| | | |
|---|---|---|
| JP | 2007-075155 A | 3/2007 |
| JP | 2009-175227 A | 8/2009 |
| JP | 2010-124242 A | 6/2010 |
| JP | 2012-137822 A | 7/2012 |
| JP | 2013-137750 A | 7/2013 |
| KR | 10-0931947 B1 | 12/2009 |
| KR | 10-0963850 B1 | 6/2010 |

OTHER PUBLICATIONS

Japanese Office Action dated Jul. 14, 2015 issued in JP 2015-525677.
Japanese Office Action dated Dec. 15, 2015 issued in JP 2015-525677.
Extended Supplementary European Search Report dated May 3, 2017 in European Patent Application No. 14 86 4234.1.

* cited by examiner

ENDOSCOPIC IMAGE DISPLAY DEVICE

CROSS-REFERENCE TO RELATED APPLICATIONS

This application is a continuation of and claims priority to PCT/JP2014/074426 filed Sep. 16, 2014, which claims the benefit of and priority from Japanese Patent Application No. 2013-240726 filed Nov. 21, 2013, the entire contents of these applications are incorporated herein by reference.

BACKGROUND OF THE INVENTION

1. Field of the Invention

The present invention relates to an image display device configured to scrollably display a plurality of images in a specific display area.

2. Description of the Related Art

A variety of display methods have been proposed to display a number of images in a relatively small display area. For example, a display method that achieves both the browsability and the visual recognizability of each image by switching the display size of thumbnail images has been proposed.

In a scrollable display method, upon a switch from a mode of displaying a number of small-size images to another mode of displaying a smaller number of larger-size images, the images are typically displayed from the beginning in the switched mode irrespective of the scroll position.

In a scrollable display method, an effective technique to locate a desired image from a number of captured images is to first display the images in a mode of displaying a large number of small-size images and, as the user approaches the desired image, to switch to another mode of displaying a smaller number of larger-size images. However, if the images are displayed from the beginning in the switched mode as described above, the user again needs to search for the desired image from the beginning.

In the meantime, a plausible technique is that the user selects at least one image to be displayed in the switched mode and the images to be displayed in the switched mode are determined so as to include the selected image. However, this technique requires the user to perform a troublesome selecting operation.

SUMMARY OF THE INVENTION

To solve the above problem, an image display device according to an aspect of the present invention includes a display control unit configured to scrollably display a plurality of images to be displayed in a specific display area of a screen, and an operation receiving unit configured to receive a scroll instruction and a display mode switching instruction that are issued in response to a user operation. The display control unit carries out scroll processing on the plurality of images in response to a received scroll instruction, and carries out switching processing of switching from a first display mode to a second display mode that differs from the first display mode in terms of an image size and the number of displayed images in response to a received display mode switching instruction. When a display mode is switched, the display control unit switches a display in the display area such that, among the plurality of images in the display area displayed in the first display mode, at least one image located at a position that goes out of the display area first upon scroll in a forward direction is arranged, upon a switch to the second display mode, at a position that also goes out of the display area first upon scroll in the forward direction in the display area.

It is to be noted that any optional combinations of the above-described constituent elements and embodiments obtained by transforming what is expressed by the present invention into methods, apparatuses, systems, recording media, computer programs, and so on are also effective as other aspects of the present invention.

BRIEF DESCRIPTION OF THE DRAWINGS

Embodiments will now be described, byway of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

Figure 1:
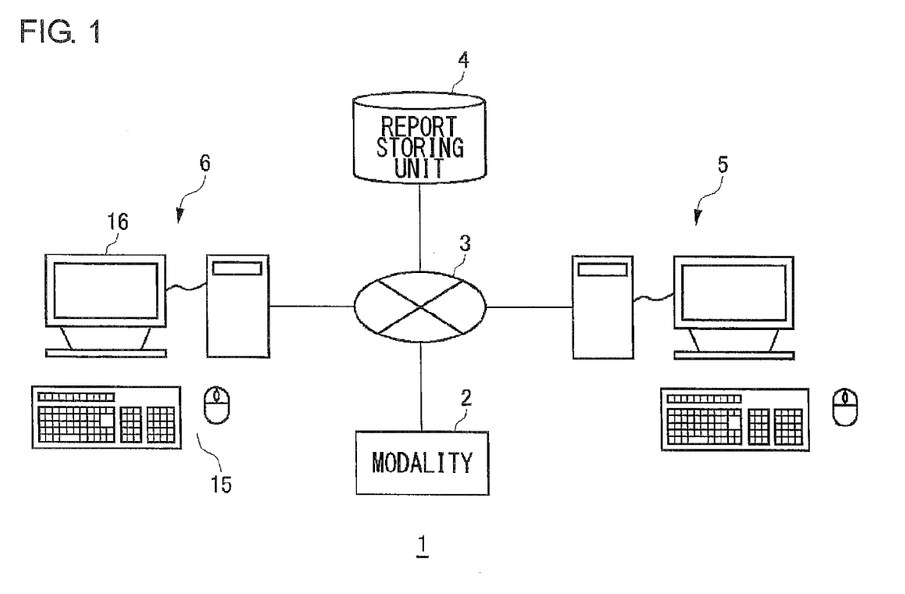
FIG. 1 schematically illustrates a configuration of a medical information management system according to an embodiment of the present invention.

FIG. 1 schematically illustrates a configuration of a medical information management system 1 according to an embodiment of the present invention. The medical information management system 1 includes a modality 2, such as an endoscope, that generates a medical image; a network 3, such as a local area network (LAN); a report storing unit 4; an order information management device 5; and a medical information input device 6.

The order information management device 5 manages order information for instructing each department to perform medical activities, such as examinations, diagnoses, and operations. The medical information input device 6 supports medical workers (hereinafter, referred to as medical professionals), such as doctors, in inputting a medical report for keeping a record of examinations and diagnostic operations. For example, an endoscopy specialist carries out an endoscopy and creates a medical report summarizing the content of observation, the content of diagnosis, the content of treatment, and so forth on the basis of the examination images. In this manner, a medical report contains information summarizing the medical knowledge of a doctor or the like and is used when providing explanations to a patient or circulated among medical professionals within a hospital. The medical information input device 6 includes, as a user interface for a medical professional, an input unit 15 and a display unit 16, which will be described later in detail. The report storing unit 4 records a medical report created by a medical professional.

Figure 2:
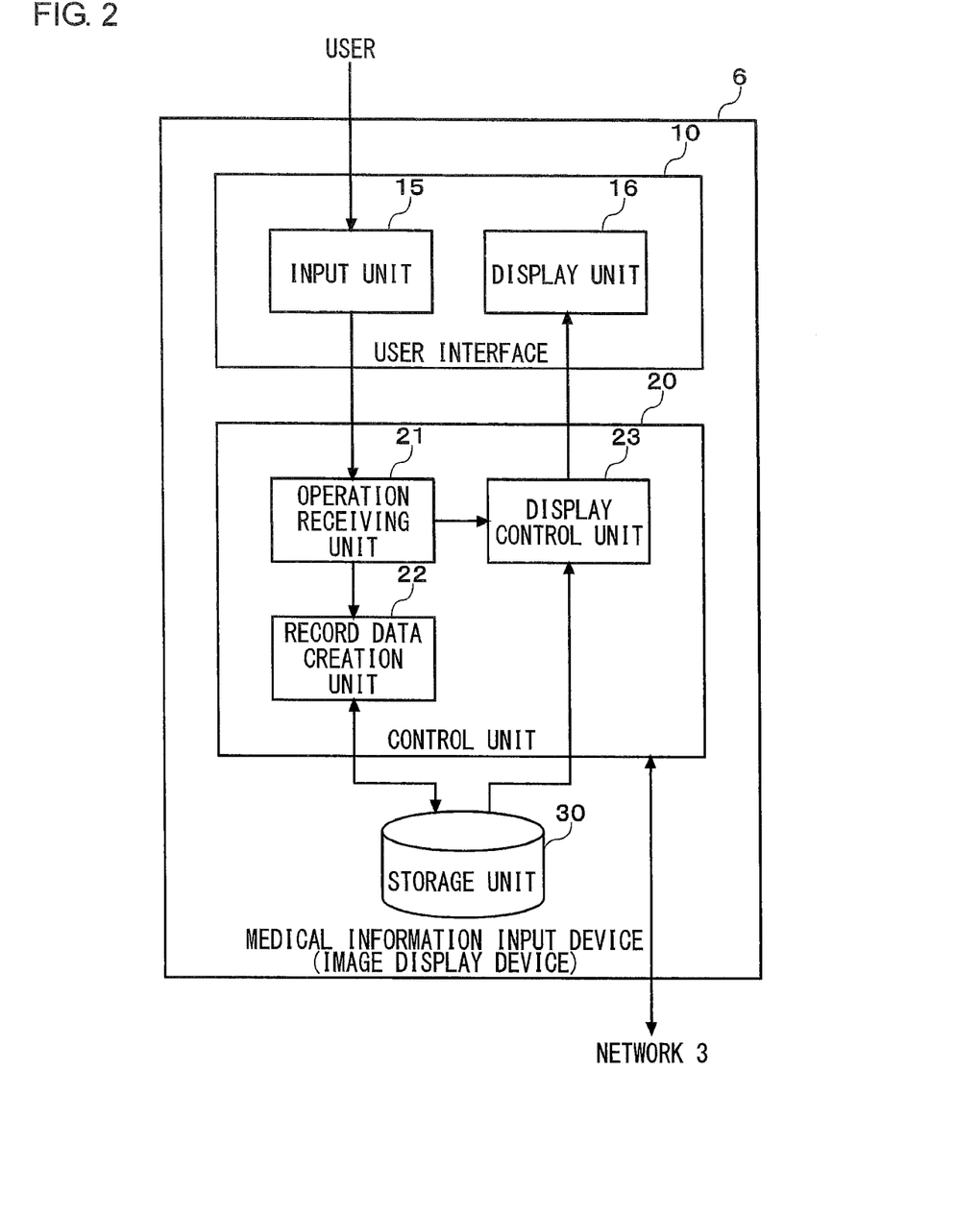
FIG. 2 schematically illustrates an internal configuration of a medical information input device illustrated in FIG. 1.

FIG. 2 schematically illustrates the internal configuration of the medical information input device 6 illustrated in FIG. 1. The medical information input device 6 includes a user interface 10, a control unit 20, and a storage unit 30. The user interface 10 includes the input unit 15 and the display unit 16. The control unit 20 includes an operation receiving unit 21, a record data creation unit 22, and a display control unit 23.

Figure 3:
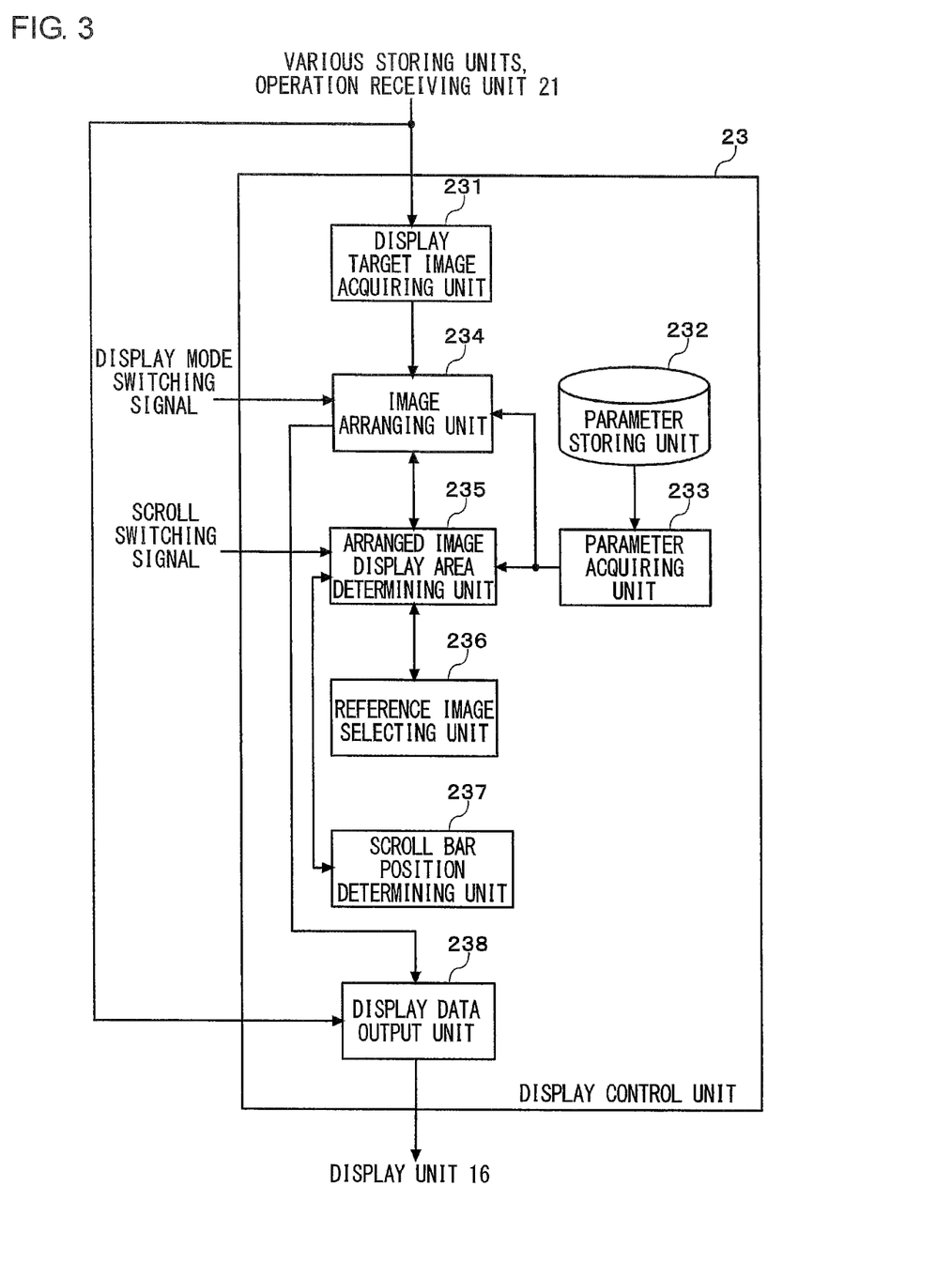
FIG. 3 schematically illustrates an internal configuration of the medical information input device illustrated in FIG. 2.

FIG. 3 schematically illustrates the internal configuration of the medical information input device 6 illustrated in FIG. 2. The display control unit 23 includes a display target image acquiring unit 231, a parameter storing unit 232, a parameter acquiring unit 233, an image arranging unit 234, an arranged image display area determining unit 235, a reference image selecting unit 236, a scroll bar position determining unit 237, and a display data output unit 238.

The components of the medical information input device 6 illustrated in FIG. 2, which includes the display control unit 23 illustrated in FIG. 3, can be implemented in hardware, such as a processor, a memory, and a large scale integration (LSI), as desired or in software, such as a program loaded onto a memory. The components are depicted herein as functional blocks implemented through cooperation of hardware and software. It is to be understood by a person skilled in the art that these functional blocks can be implemented in various forms, namely, solely in hardware, solely in software, or through a combination of hardware and software.

As described above, the medical information input device 6 has a function of generating a report input screen that allows a medical professional to keep a record of an examination and recording execution data of an examination and so on input by the medical professional into the report storing unit 4. This function is referred to as a report input function and is provided as a basic function in the medical information input device 6 for keeping a record of the result of medical activities.

Figure 4:
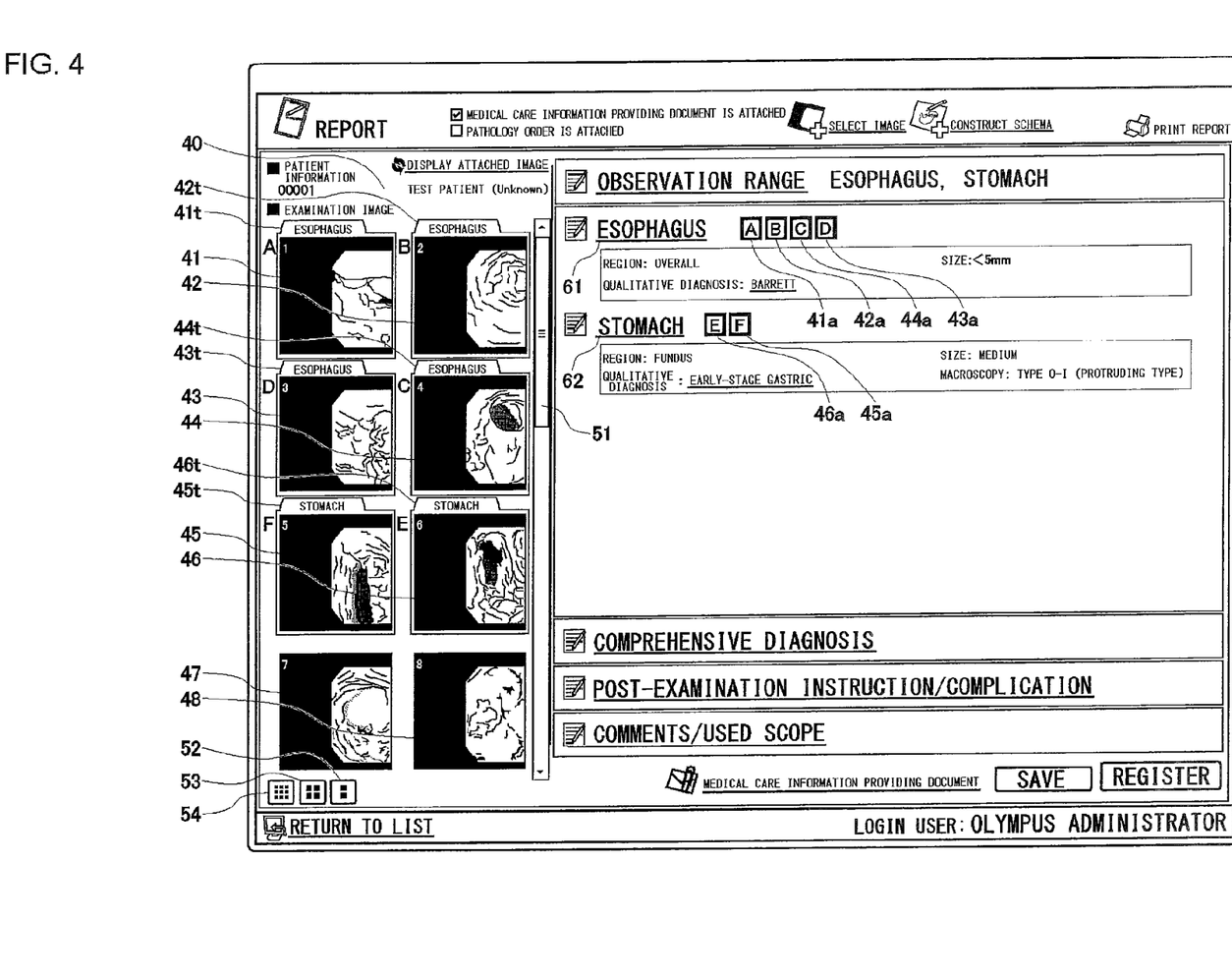
FIG. 4 illustrates an example of a report input screen of a medical information input device according to an embodiment of the present invention.

FIG. 4 illustrates an example of the report input screen of the medical information input device 6 according to an embodiment of the present invention. The report input screen illustrated in FIG. 4 is a report input screen of an endoscopy. An image captured through the endoscopy can be attached to the report. As indicated in an upper column and a lower column of the report input screen illustrated in FIG. 4, a medical care information providing document is attached. A pathology order is not attached.

In a left column of the report input screen illustrated in FIG. 4, patient information and examination images are displayed. A plurality of examination images are displayed in an image display area 40. The examination images are acquired from an image storing unit (not illustrated) of the medical information management system 1. This image storing unit stores patient images captured by the modality 2. The images are each provided with a patient ID and an examination ID and are stored in the order in which the images are captured in respective examinations. A medical professional inputs a patient ID and an examination ID through the input unit 15 in a previous screen of the report input screen, and the patient information and the examination images illustrated in FIG. 4 are retrieved from the aforementioned image storing unit, a patient information storing unit (not illustrated), and an examination information storing unit (not illustrated). Part of the retrieved examination information is embedded into the corresponding items in a right column illustrated in FIG. 4. The image storing unit, the patient information storing unit, and the examination information storing unit may be constructed in a recording medium in which the report storing unit 4 is constructed or may be constructed in a different recording medium.

In the right column of the report input screen, the items on which reports are to be input are displayed. In FIG. 4, the displayed items are the observation range, the comprehensive diagnosis, the post-examination instruction/complication, and the comments/used scope. The observation range accepts an input of the content of observation, the content of diagnosis, and the content of treatment for each region of a human body. The comprehensive diagnosis accepts an input of the content of comprehensive diagnosis. The post-examination instruction/complication accepts an input of the content of instructions from the doctor after the examination and the presence or absence of any complications. The comments/used scope accepts an input of comments other than those indicated under the above items and the type of the scope used in the examination.

In FIG. 4, the content of observation, the content of diagnosis, and the content of treatment on two regions, that is, an esophagus 61 and a stomach 62 are input under the observation range. Under the esophagus 61, an image A 41a, an image B 42a, an image C 44a, and an image D 43a selected from the image display area 40 are attached as examination images of the esophagus. In a similar manner, under the stomach 62, an image E 46a and an image F 45a selected from the image display area 40 are attached as examination images of the stomach.

When a medical professional selects an examination image and adds the image under the observation range, the operability for the medical professional increases if the captured images and the report input areas are displayed in a list form. Therefore, the image display area 40 is desirably laid out basically in a size of no greater than one-third to one-half the size of the entire screen. Meanwhile, a number of images may be captured in a single endoscopy. In addition, the current examination images and the past examination images of the same patient may both be displayed to compare the current examination images with the past examination images. In such cases, approximately 50 to 100 images, for example, may be displayed in the image display area 40. If the entire images are displayed at once in the image display area 40 in the aforementioned case, the display size of each image becomes too small.

Thus, it is plausible to display the images to be displayed in the image display area 40 in a paginated display format or in a scrollable display format. Endoscopic examination images are obtained by imaging the internal cavity of a patient in time series. Thus, an image of interest to the doctor is desirably displayed concurrently with the images preceding and following the aforementioned image in a single screen. For example, observing images of close regions at the same time makes it possible to diagnose any foreign object captured in the images with higher reliability. A plurality of examination images are not paginated in accordance with the captured regions and are obtained by imaging the internal cavity successively. Thus, a scrollable display is more desirable than a paginated display. Accordingly, in the present embodiment, a plurality of examination images are scrollably displayed in the image display area 40.

In FIG. 4, a scroll bar 51 is provided at the right end of the image display area 40. In addition, eight images 41 to 48 are displayed in an arrangement of 4 rows by 2 columns within the image display area 40. The images 41 to 44 are being selected as the attached images of the esophagus 61, and tabs 41t to 44t each marked as "esophagus" are added to the upper ends of the respective images 41 to 44. The images 45 and 46 are being selected as the attached images of the stomach 62, and tabs 45t and 46t each marked as "stomach" are added to the upper ends of the respective images 45 and 46. The doctor can switch the images to be displayed in the image display area 40 by moving up or down the scroll bar 51 using an input device, such as a mouse and up and down keys.

The doctor may want to enlarge and observe an image in which a lesion may be captured. In addition, the doctor may want to reach a target image quickly by scrolling faster. The doctor who has captured the images of the internal cavity of the patient with an endoscope knows to some extent intuitively approximately where in the sequentially captured images the image of a region of interest is located. Accordingly, in the present embodiment, a plurality of display modes that each differ in terms of the image size and the number of display columns are defined. When the image size is reduced and the number of display columns is increased, the visual recognizability of each image decreases, but the scrolling speed increases. On the other hand, when the image size is increased and the number of display columns is reduced, the scrolling speed decreases, but the visual recognizability of each image increases.

In the present embodiment, three display modes, namely, a one-column display mode, a two-column display mode, and a three-column display mode are defined, and the design that allows the display mode to be switched as desired in accordance with a user operation is employed. In FIG. 4, a one-column display button 52, a two-column display button 53, and a three-column display button 54 are provided near the lower end of the image display area 40. The user can switch the display mode to a desired display mode by pressing one of the display buttons 52 to 54 through a mouse click or the like.

Upon finishing creating a report, the doctor presses the register button in the lower right column of the report input screen. The record data creation unit 22 of the medical information input device 6 records the report data into the report storing unit 4 through the network 3.

Hereinafter, the attention is directed herein to the switching of the display mode of the images displayed in the report input screen. In other words, the attention is directed to a function of the medical information input device 6 as an image display device, with reference to FIG. 2 again.

The input unit 15 of the user interface 10 includes an input device, such as a keyboard and a mouse, and generates an instruction signal corresponding to a user operation. The input unit 15 outputs a generated instruction signal to the control unit 20. The display unit 16 includes a display device, such as a liquid crystal display, and displays display data input from the control unit 20. If a touch panel display is used, a display thereof functions as an input device as well.

The control unit 20 controls the medical information input device 6 as a whole. In the present embodiment, the attention is directed to functions related to a report input screen display function and a report creating function, and descriptions on other functions are omitted. The operation receiving unit 21 receives an instruction signal generated by the input unit 15 in response to a user operation. Upon receiving text data related to the content of the report input by the doctor, the operation receiving unit 21 outputs the text data to the record data creation unit 22 and the display control unit 23. Upon the doctor selecting an examination image and associating the image with the observation range of a given region, the operation receiving unit 21 outputs the selection information and the association information of that image to the record data creation unit 22 and the display control unit 23.

In addition, upon receiving an instruction signal issued in response to a user operation related to an image display in the image display area 40, the operation receiving unit 21 outputs the received instruction signal to the display control unit 23. For example, upon receiving a scroll switching signal and a display mode switching signal, the operation receiving unit 21 outputs these signals to the display control unit 23.

The record data creation unit 22 acquires report input form data from the storage unit 30 and acquires input data related to report creation from the operation receiving unit 21. In addition, the record data creation unit 22 acquires a selected image from the image storing unit, acquires patient information from the patient information storing unit, and acquires examination information from the examination information storing unit. The record data creation unit 22 generates report data by embedding the acquired pieces of data in the respective columns of the acquired report input form. Instead of directly embedding the image, the record data creation unit 22 may embed link data indicating a location where the image is stored. The record data creation unit 22 records the regenerated report data into the report storing unit 4 through the network 3.

The display control unit 23 controls the display format of the images in the image display area 40. When the number of images to be displayed exceeds the number of images that can be displayed in the image display area 40, the display control unit 23 displays the scroll bar 51 in the image display area 40. When the number of images to be displayed does not exceed the number of images that can be displayed in the image display area 40, the display control unit 23 displays the entire images to be displayed in the image display area 40 in a list form.

Upon a scroll switching instruction being input from the operation receiving unit 21, the display control unit 23 scrolls through the plurality of images displayed in the image display area 40 in response to the switching instruction. In the present embodiment, scroll in the vertical direction as illustrated in FIG. 4 is assumed. If a mouse with a wheel is used as an input device, an operation of rolling the wheel back and forth with an index finger is intuitively associated with vertical scroll. Therefore, when the scroll bar 51 is to be moved with the wheel on the mouse, the vertical scroll may have higher operability than the horizontal scroll.

Upon a display mode switching instruction being input from the operation receiving unit 21, the display control unit 23 switches the display method of the images in the image display area 40 in response to the display mode switching instruction. In the example described above, the display control unit 23 switches the display mode among the three display modes, namely, the one-column display mode, the two-column display mode, and the three-column display mode. The number of display modes is not limited to three and may be two or four or more. Hereinafter, with regard to the two display modes employed before and after the switching, the display mode employed before the switching is referred as a first display mode, and the display mode employed after the switching is referred to as a second display mode.

Upon the operation receiving unit 21 receiving a display mode switching instruction in the middle of scrolling, the display control unit 23 carries out the following processing.

Specifically, the display control unit 23 switches the display in the image display area 40 such that, among the plurality of images displayed in the image display area 40 in the first display mode, at least one image located at a position that goes out of the image display area 40 first upon scroll in a forward direction is arranged, upon a switch to the second display mode, at a position that also goes out of the image display area 40 first upon scroll in the forward direction in the image display area 40.

In the case of typical vertical scroll, the forward direction is the downward direction, and the backward direction is the upward direction. The directions may be designed in an opposite manner. In the case of typical vertical scroll, an image located at a position that goes out of the image display area 40 next upon scroll in the forward direction is an image located in the uppermost row of the image display area 40. In the case of typical horizontal scroll, the forward direction is the right direction, and the backward direction is the left direction. The directions may be designed in an opposite manner. In the case of typical horizontal scroll, an image located at a position that goes out of the image display area 40 next upon scroll in the forward direction is an image located in the leftmost column of the image display area 40.

In the case of typical vertical scroll, the display control unit 23 switches the display in the image display area 40 such that the image at the upper left end of the image display area 40 displayed in the first display mode is displayed in the uppermost row of the image display area 40 upon a switch to the second display mode. When a plurality of images to be displayed are stored in the order in which the images are captured, the plurality of images are arranged basically in the order in which the images are captured. In a display method with typical vertical scroll, the images are arranged successively from the left to the right and flow down to the next row upon reaching the right end, and this process is repeated. Therefore, the image at the upper left end is the image captured first among the sequentially captured images.

In general, among the plurality of images that are displayed in the image display area 40 in the first display mode such that the images are arranged in the temporally forward direction with the first image among the sequentially captured images serving as the origin, the display control unit 23 displays images in a number that can be displayed in the second display mode in the image display area 40 upon a switch to the second display mode. There is a case in which some images in the temporally backward direction with the first image among the sequentially captured images serving as the origin are also included. An example in which images in the temporally backward direction are included will be described later.

In addition, when a portion of the images in the uppermost row of the image display area 40 displayed in the first display mode is outside the image display area 40, the display control unit 23 regards these images in the uppermost row as not being present and switches the display mode. Specifically, the display control unit 23 switches the display in the image display area 40 such that the image at the left end among the images in a row subsequent to the uppermost row is displayed in the uppermost row of the image display area 40 upon a switch to the second display mode. A specific example of a case in which a portion of the images in the uppermost row is outside the image display area 40 will be described later. Hereinafter, details of display mode switching processing will be described in concrete terms.

Figure 5:
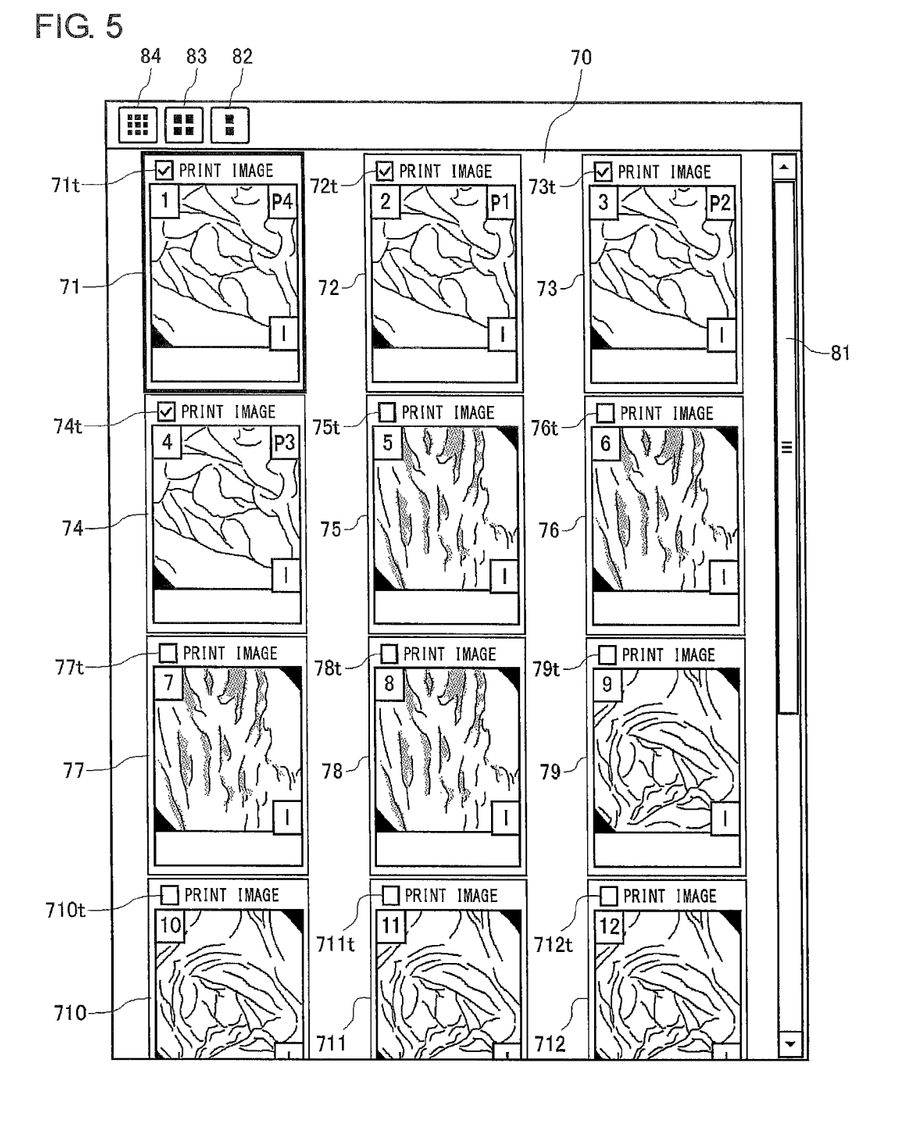
FIG. 5 illustrates a first display example of a plurality of images displayed in an image display area.
Figure 6:
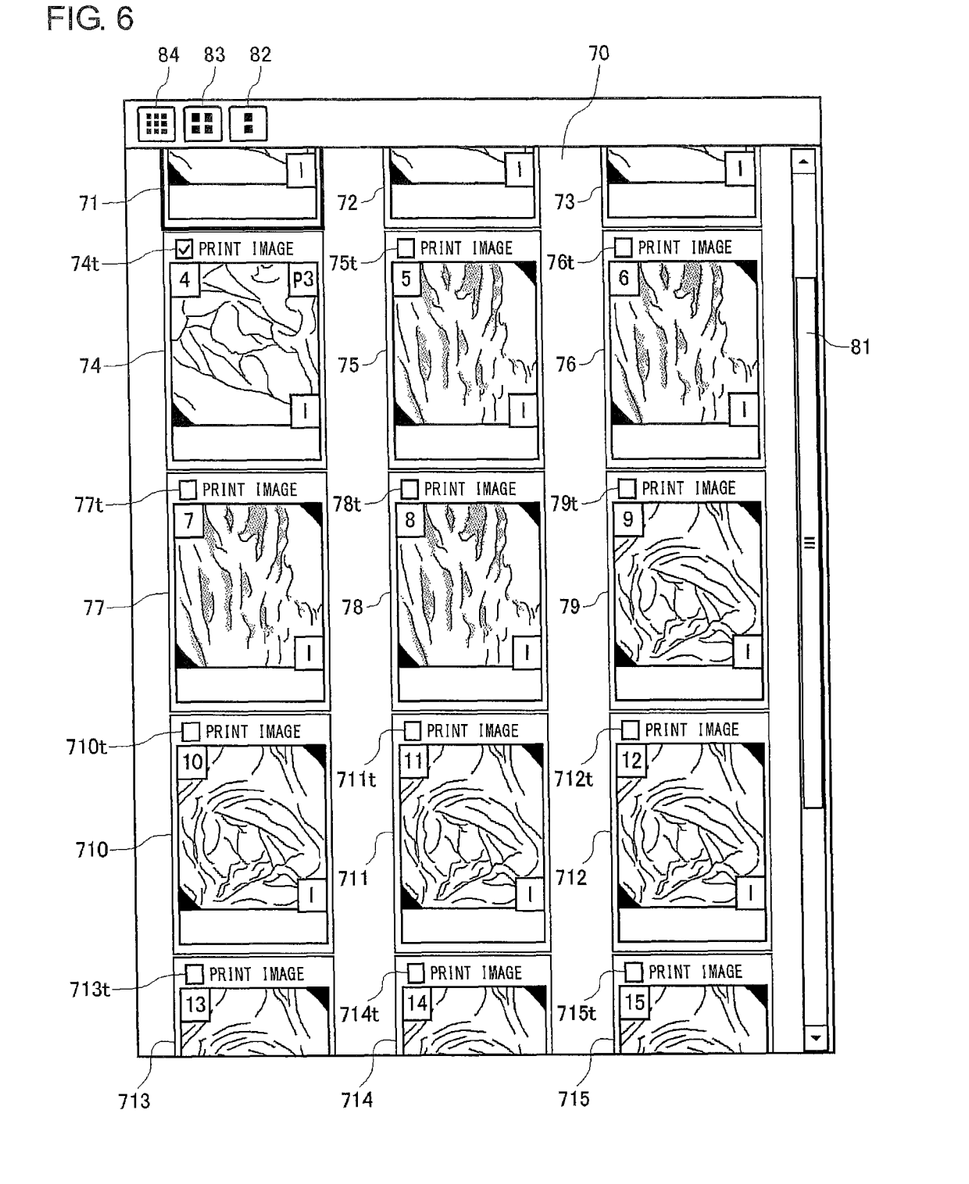
FIG. 6 illustrates a second display example of a plurality of images displayed in an image display area.
Figure 7:
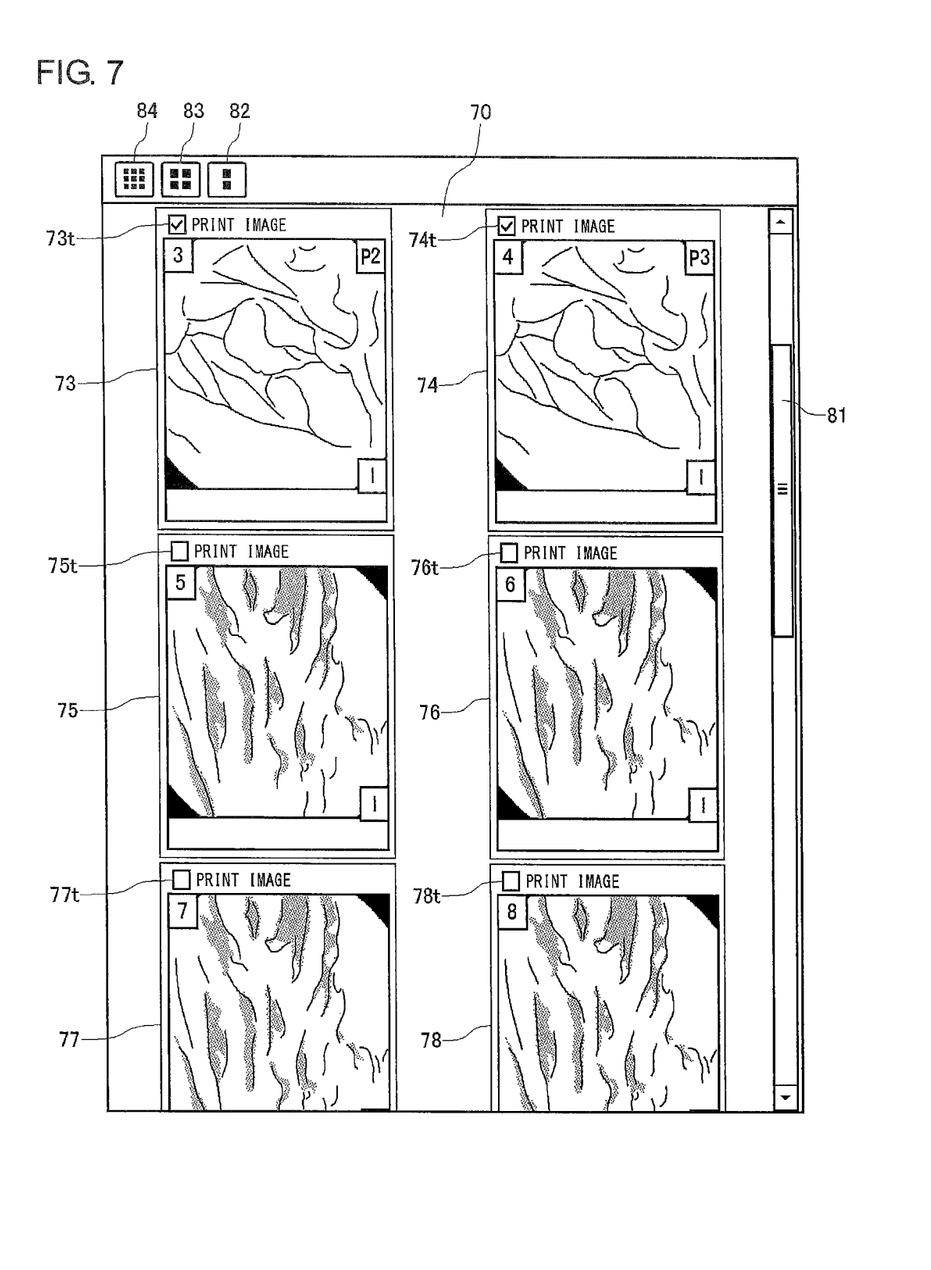
FIG. 7 illustrates a third display example of a plurality of images displayed in an image display area.

FIG. 5 illustrates a first display example of a plurality of images 71 to 712 displayed in an image display area 70. FIG. 6 illustrates a second display example of a plurality of images 71 to 715 displayed in the image display area 70. FIG. 7 illustrates a third display example of a plurality of images 71 to 78 displayed in the image display area 70. The image display area 70 illustrated in FIGS. 5 to 7 is basically the same as the image display area 40 illustrated in FIG. 4 but differs in some respects. First, although the one-column display button 52, the two-column display button 53, and the three-column display button 54 are provided near the lower end of the image display area 40 in FIG. 4, in FIGS. 5 to 7, a one-column display button 82, a two-column display button 83, and a three-column display button 84 are provided near the upper end of the image display area 70. In addition, in FIGS. 5 to 7, a tab including a checkbox for specifying whether the image is to be printed is formed at the upper end of each image.

In the initial state, the display control unit 23 displays the plurality of images to be displayed in a display mode that allows a maximum number of images to be displayed. In the present embodiment, the display control unit 23 displays the images in the three-column display mode. A maximum number of images that can be displayed in the image display area 70 are displayed first so that the user can quickly locate a desired image.

In FIG. 5, a first tab 71t to a twelfth tab 712t each including the above-described checkbox are formed at the upper ends of the first image 71 to the twelfth image 712, respectively, displayed in the image display area 70. In FIG. 5, the first tab 71t to the fourth tab 74t of the first image 71 to the fourth image 74, respectively, are checked. When printing is executed in this state, the first image 71 to the fourth image 74 are printed.

The tabs illustrated in FIG. 5, which each include the checkbox for specifying whether the image is to be printed, may also include another checkbox for specifying another process is to carried out. For example, a checkbox for specifying whether the image is to be attached to the report may be provided. In addition, a checkbox for specifying whether an enlarged image is to be displayed in a pop-up window may be provided.

Upon receiving an image selection instruction issued in response to a user operation of selecting an image to be processed, the operation receiving unit 21 outputs the image selection instruction to the display control unit 23. Such processing includes printing the image, attaching the image, displaying the enlarged image in a pop-up window, and deleting the image. The display control unit 23 switches the display in the image display area 70 irrespective of image selection that is based on the image selection instruction.

The display control unit 23 selects, among the first image 71 to the twelfth image 712 displayed in the image display area 70, the first image 71, which is located at the upper left end and is the oldest image in the arranged order, as the reference image to be used when the display mode is switched. In the display examples illustrated in FIGS. 5 to 7, six images can be displayed in the image display area 70, as illustrated in FIG. 7, in the two-column display mode. In the one-column display mode, two images can be displayed in the image display area 70. When the display mode is switched from the three-column display mode as in the state illustrated in FIG. 5 to the two-column display mode, the display control unit 23 initially displays six images, namely, the first image 71 serving as the reference image, the second image 72, the third image 73, the fourth image 74, the fifth image 75, and the sixth image 76 in the temporally forward direction in the image display area 70 upon a switch to the two-column display mode. When the display mode is switched to the one-column display mode, the display control unit 23 initially displays two images, namely, the first image 71 serving as the reference image and the second image 72 located in the temporally forward direction in the image display area 70 upon a switch to the one-column display mode. In this display mode switching processing, the display control unit 23 does not take the presence of checks in the checkboxes into consideration.

FIG. 6 illustrates a state in which a scroll bar 81 has been moved downward from the state illustrated in FIG. 5, the plurality of images displayed in the image display area 70 have been scrolled down, and the first image 71 to the fifteenth image 715 are displayed. In FIG. 6, only the lower portions of the first image 71 to the third image 73 are displayed, and the upper portions and the middle portions of these images are missing from the display. In the present embodiment, to be selected as the above-described reference image, an image should have no portion missing from the display. Therefore, the first image 71 is not selected as the reference image. When a determination as to whether an image has a missing portion is made, the tab may be regarded as part of the image or as being separate from the image.

In addition, an image may be determined to have a missing portion if even a single pixel of that image is not included in the image display area 70, or an image may be determined to have a missing portion if a set number of pixels or more of that image are not included in the image display area 70. For example, an image may be determined not to have a missing portion if the number of pixels that are not included in the image display area 70 is less than the number of pixels corresponding to three lines. In the present embodiment, the image that is displayed at the upper left end before the display mode is switched is displayed in the uppermost row upon the display mode being switched. When an image displayed in the uppermost row in the image display area 70 before the display mode is switched is displayed substantially adjacent to the upper end of the image display area 70, that image may go out of the image display area 70 even if the user intends to keep that image in the image display area 70 when the display mode is switched. When there is a certain margin in determining whether an image has a missing portion as described above, the image displayed at the upper left end before the display mode is switched can be prevented from going out of the image display area 70 against the user's intention when the display mode is switched.

The display control unit 23 regards the first image 71 to the third image 73 and the thirteenth image 713 to the fifteenth image 715 each having a missing portion as not being present in the processing of selecting the reference image. The display control unit 23 selects, among the fourth image 74 to the twelfth image 712 displayed in the image display area 70, the fourth image 74, which is located at the upper left end and is the oldest image in the arranged order, as the reference image.

When the display mode is switched from the three-column display mode as in the state illustrated in FIG. 6 to the two-column display mode, it is plausible that the display control unit 23 initially displays six images, namely, the fourth image 74 serving as the reference image, the fifth image 75, the sixth image 76, the seventh image 77, the eighth image 78, and the ninth image 79 in the temporally forward direction upon a switch to the two-column display mode. If the fourth image 74 is displayed at the upper left end in this manner, the second image 72 and the third image 73 are arranged in a row above the row in which the fourth image 74 and the fifth image 75 are arranged, and a blank space and the first image 71 are arranged in a row above the row in which the second image 72 and the third image 73 are arranged. When the user moves the scroll bar 81 to the uppermost position, this blank space in the top row is displayed.

To eliminate this blank space in the top row, odd-numbered images need to be arranged in the left column, and even-numbered images need to be arranged in the right column. In accordance with this arrangement, the first image 71 and the second image 72 are arranged in the top row, and the third image 73 and the fourth image 74 are arranged in a row below the top row. As illustrated in FIG. 7, the display control unit 23 displays the row that contains the fourth image 74 serving as the reference image in the uppermost row of the image display area 70. Therefore, instead of displaying the sixth images, namely, the fourth image 74 serving as the reference image, the fifth image 75, the sixth image 76, the seventh image 77, the eighth image 78, and the ninth image 79 in the temporally forward direction, the display control unit 23 displays the six images including five images, namely, the fourth image 74, the fifth image 75, the sixth image 76, the seventh image 77, and the eighth image 78 in the temporally forward direction and the third image 73 in the temporally backward direction from the fourth image 74.

To eliminate a blank space in the top row when the display mode is switched in this manner, the display control unit 23 arranges the images from the left end of the uppermost row and displays the row that contains the reference image in the uppermost row of the image display area 70. Alternatively, if a blank space is permitted in the uppermost row when the display mode is switched, the display control unit 23 arranges the reference image at the left end of the uppermost row of the image display area 70 and arranges the remaining images so as to precede or follow the reference image. The designer may select either display method. Alternatively, the user may be allowed to select a display method.

Hereinafter, with reference to FIG. 3, the function of the display control unit 23 will be described in more concrete terms. The display target image acquiring unit 231 acquires a plurality of images, which serve as images to be displayed, captured in a given examination from the aforementioned image storing unit. The display target image acquiring unit 231 may simultaneously acquire images of the same patient that have been captured in a previous examination.

The parameter storing unit 232 stores parameters of each display mode. Specifically, the parameter storing unit 232 stores the image size per image, the number of display columns, and the interval between images in each display mode. The parameter storing unit 232 also stores the size of the image display area. The size of the image display area is the same among the display modes. The parameter acquiring unit 233 acquires parameter values of a specified display mode from the parameter storing unit 232.

The image arranging unit 234 arranges the plurality of images to be displayed supplied from the display target image acquiring unit 231 in a work memory in accordance with the specified display mode. This work memory can be constructed in the storage unit 30. The initial display mode is set in advance. In the present embodiment, the initial display mode is set to the three-column display mode. A display mode to be switched to is specified by a display mode switching signal from the operation receiving unit 21.

The image arranging unit 234 arranges the images in accordance with the parameters acquired by the parameter acquiring unit 233.

The arranged image display area determining unit 235 determines a display area to be displayed in the image display area 70 for the images arranged in the work memory. The size of this display area is determined in accordance with the parameter values that the parameter acquiring unit 233 has acquired from the parameter storing unit 232. In the initial state, the arranged image display area determining unit 235 determines the position of the display area such that the upper side of the arranged images substantially coincides with the upper side of the display area. Thereafter, upon receiving a scroll switching signal from the operation receiving unit 21, the arranged image display area determining unit 235 changes the position of the display area in accordance with the scroll switching signal. In the present embodiment, the vertical scroll is employed, and thus the display area of the arranged images is moved up or down in accordance with the scroll switching signal.

The reference image selecting unit 236 selects the image located at the upper left end of the display area as the reference image and supplies the selected image to the arranged image display area determining unit 235. Upon the display mode being switched, the arranged image display area determining unit 235 determines the position of the display area such that the reference image is displayed in the uppermost row of the display area. The scroll bar position determining unit 237 determines the display position of the scroll bar in accordance with the position of the display area moved by the arranged image display area determining unit 235.

The display data output unit 238 acquires report input form data from the storage unit 30, acquires input data from the operation receiving unit 21, acquires patient information from the patient information storing unit, and acquires examination information from the examination information storing unit. In addition, the display data output unit 238 acquires images to be displayed in the display area determined by the arranged image display area determining unit 235 from the work memory. The display data output unit 238 generates display data to be displayed in the display unit 16 on the basis of the above-described pieces of data and outputs the generated display data to the display unit 16.

Figure 8:
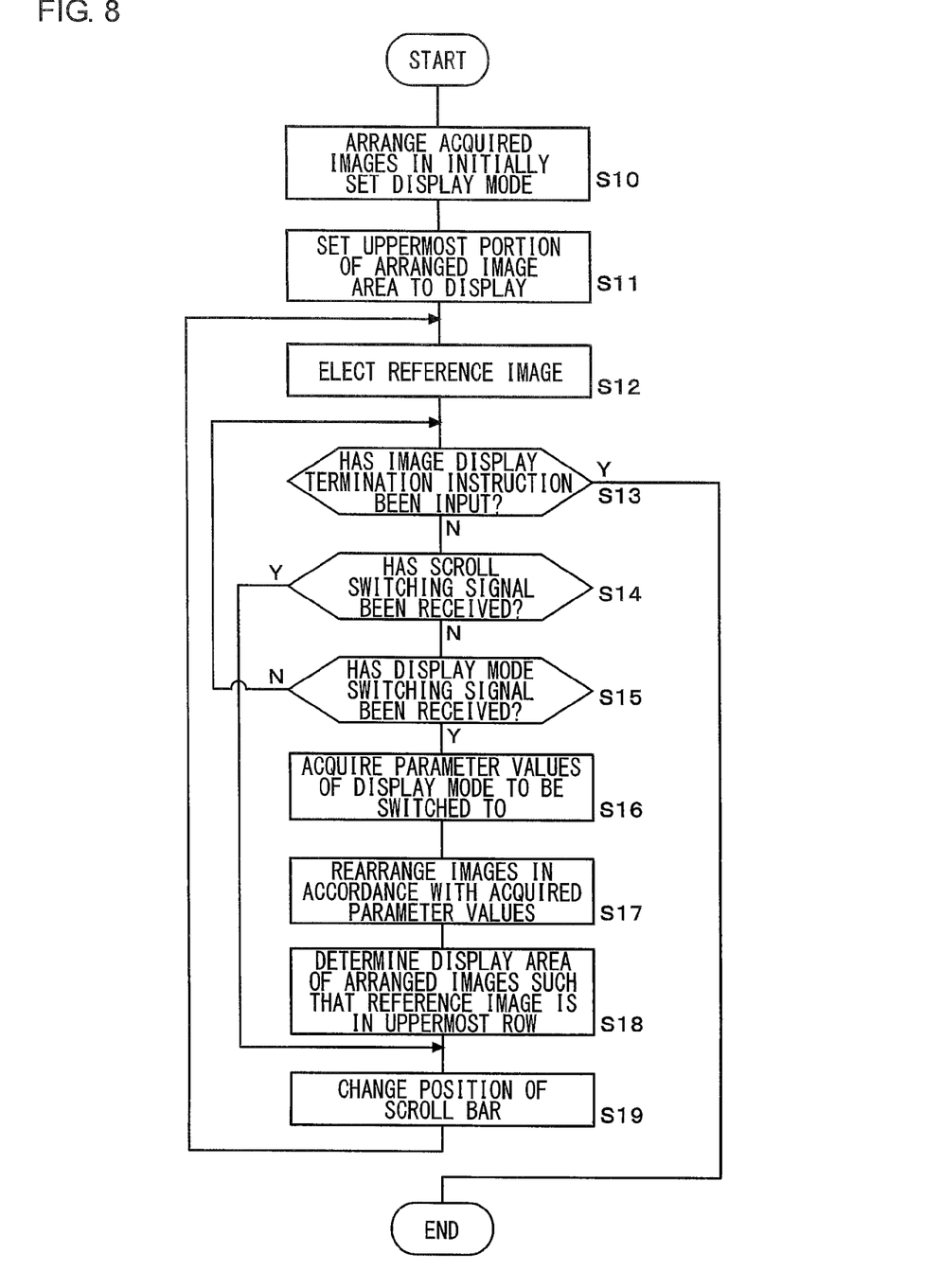
FIG. 8 is a flowchart illustrating an operation of a display control unit illustrated in FIG. 3.

FIG. 8 is a flowchart illustrating the operation of the display control unit 23 illustrated in FIG. 3. The image arranging unit 234 arranges the plurality of images to be displayed supplied from the display target image acquiring unit 231 in the work memory in the initially set display mode (S10). The arranged image display area determining unit 235 sets the uppermost portion of the arranged images to the display area that is actually displayed in a screen (S11). The reference image selecting unit 236 selects the image located at the upper left end of the display area as the reference image (S12). If an instruction to terminate the image display in the display area is input (Y in S13), the entire processing is terminated.

Upon the arranged image display area determining unit 235 receiving a scroll switching signal (Y in S14), the processing proceeds to step S19. The scroll bar position determining unit 237 changes the position of the scroll bar in accordance with the received scroll switching signal and the current position of the display area (S19). Thereafter, the processing returns to step S12.

Upon the image arranging unit 234 receiving a display mode switching signal (Y in S15), the parameter acquiring unit 233 acquires parameter values, such as the image size and the number of display columns in the display mode to be switched to, from the parameter storing unit 232 (S16). The image arranging unit 234 rearranges the plurality of images in the work memory in accordance with the parameter values of the display mode to be switched to (S17). The arranged image display area determining unit 235 determines the position of the display area of the rearranged images such that the reference image selected in step S12 is displayed in the uppermost row (S18). The scroll bar position determining unit 237 changes the position of the scroll bar in accordance with the position of the changed display area (S19). Thereafter, the processing returns to step S12. If no scroll switching signal is received (N in S14) and no display mode switching signal is received (N in S15), the processing returns to step S13.

As described above, according to the image processing device with a scrollable display of the present embodiment, when the display mode is switched, images to be initially displayed in a display mode to be switched to are determined such that the image displayed at the upper left end before the display mode is switched is displayed in the uppermost row upon the display mode being switched. Accordingly, when a plurality of images are scrollably displayed, a user's desired image can be displayed initially when the mode is switched. In this case, a troublesome operation of specifying an image to be displayed or the like is not necessary.

When a plurality of images are scrollably displayed, an operation of moving the scroll bar in one direction (downward direction in the present embodiment) is simpler than an operation of moving the scroll bar in two directions (upward and downward directions in the present embodiment). When the user carries out an operation of switching the display mode from a mode of displaying a large number of small-size images to a mode of displaying a smaller number of large-size images, this operation indicates that an image of interest is present among the images displayed at that moment. When the oldest image among the images displayed before the display mode is switched is displayed in the uppermost row after the display mode is switched as in the present embodiment, the entire images displayed before the display mode is switched can be viewed in a larger size only with a downward scrolling operation.

In place of the switching method according to the present embodiment, plausible processing is that the user is allowed to specify, before the display mode is switched, an image to be displayed at the top or at the center after the display mode is switched. This, however, creates an additional operation for the user. Alternatively, it is plausible that the image display is switched such that the image displayed at the center among the images displayed before the display mode is switched is also displayed at the center after the display mode is switched. However, the image of interest to the user may precede or follow the center image, and thus the user may need to scroll upward or downward.

The switching method according to the present embodiment is effective especially in a case in which a plurality of images are arranged in the order in which the images are captured. The plurality of images can be displayed sequentially with a downward scrolling operation in the temporally forward direction in the order in which the images are captured. The user scrolls quickly to the vicinity of a target image on the basis of his or her memory of the time at which the images are captured, and upon reaching the vicinity of the target image, the user switches to the display mode in which the images are displayed in a larger size. The user can thus reach the target image only with the downward scrolling operation.

Thus far, an embodiment of the present invention has been described. This embodiment is merely illustrative, and it may be appreciated by a person skilled in the art that various modifications can be made to the combinations of the components and the processing processes and such modifications also fall within the scope of the present invention.

In the preceding description, an example in which the display area to which the display mode switching method according to the present embodiment is applied is arranged in a portion of the report creation screen has been illustrated. With respect to this point, a screen in which the display area to which the display mode switching method according to the present embodiment is applied is not limited to the report creation screen. The display area may be displayed in a portion of a screen for creating other medical documents, such as an electronic medical record. When creating a medical document, such as an electronic medical record, the doctor can create the medical document while checking a medical image displayed in the creation screen. In addition, although an examination image captured with an endoscope is illustrated as an example of a medical image in the preceding description, a medical image may be an image captured by a different medical device, such as a CT and an MRI.

In addition, the image display method that employs the display mode switching method according to the present embodiment can be applied not only to a screen for creating a medical document but also to an image display in general that scrollably displays a plurality of images. In particular, the image display method is suitable for use in a device having a small-size screen that is likely to render the scrollable display necessary. For example, the display method may be applied to a display of a digital camera, a feature phone, a smartphone, or a portable game console when a plurality of images are to be scrollably displayed.

In the preceding description, an example in which the screen is vertically scrolled from the top and downward has been illustrated. With respect to this point, the display mode switching method according to the present embodiment can also be applied in a case in which the screen is scrolled horizontally from the left to the right. In that case, the display control unit 23 carries out scroll processing in the horizontal direction on the plurality of images to be displayed, and carries out switching processing of switching from the first display mode to the second display mode that differs from the first display mode in terms of the number of display rows in response to a received display mode switching instruction. Specifically, the display control unit 23 switches the display in the display area such that the image at the upper left end of the display area displayed in the first display mode is arranged in the leftmost column of the display area upon a switch to the second display mode. In addition, if a portion of the images in the leftmost column of the display area displayed in the first display mode is outside the display area when the operation receiving unit 21 receives a display mode switching instruction, the display control unit 23 switches the display in the display area such that the image at the top among the images in a column next to the leftmost column is arranged in the leftmost column of the display area upon a switch to the second display mode. In addition, the display mode switching method according to the present embodiment can also be applied in a case in which the screen is scrolled horizontally from the right to the left. In that case, the display control unit 23 switches the display in the display area such that the image at the upper right end of the display area displayed in the first display mode is displayed in the rightmost column of the display area upon a switch to the second display mode.

What is claimed is:

1. An endoscopic image display device, comprising:
a processor comprising hardware, wherein the processor is configured to:
control a screen to scrollably display a plurality of images in a first display mode,
wherein in the first display mode, the plurality of images are scrollably displayed in a first arrangement in a specific display area in the screen, and
wherein in the first display mode, a reference image of the plurality of images is displayed at a position in the first arrangement that goes out of the specific display area first upon scroll in a forward direction from a scroll position that is forward of a beginning position of a scrolling range of the first arrangement; and
in response to receiving a display mode switching signal, control the screen to scrollably display the plurality of images in a second display mode,
wherein in the second display mode, the plurality of images are scrollably displayed in a second arrangement in the specific display area in the screen, wherein the second arrangement is different from the first arrangement, and
wherein in the second display mode, the screen is controlled to display the reference image at a position in the second arrangement that goes out of the specific display area first upon scroll in the forward direction.

2. The endoscopic image display device according to claim 1,
wherein the first arrangement is any one arrangement of M (M is an integer equal to or greater than 3) rows by 3 columns, M rows by 2 columns, and M rows by 1 column, and
wherein the second arrangement is any one arrangement of M rows by 3 columns, M rows by 2 columns, and M rows by 1 column, the first arrangement being different from the second arrangement.

3. The endoscopic image display device according to claim 1,
wherein the processor is configured to carry out scrolling of the plurality of images in the first display mode and the second display mode in a vertical direction,
wherein the second display mode is different from the first display mode in terms of the number of display columns of the plurality of images displayed,
wherein in the first display mode, the processor is configured to display the reference image at an upper left end of the specific display area, and
wherein in the second display mode, the processor is configured to display the reference image in an uppermost row of the specific display area.

4. The endoscopic image display device according to claim 3,
wherein in the first display mode, if a portion of an image at the uppermost row of the specific display area displayed is outside the specific display area the processor is configured to set an image of the plurality of images at a left end among images in a row subsequent to the uppermost row as the reference image, and
wherein in the second display mode, the screen is controlled to display the reference image in an uppermost row of the specific display area.

5. The endoscopic image display device according to claim 1,
wherein the processor is configured to carry out scrolling of the plurality of images in the first display mode and the second display mode in a horizontal direction, wherein the second display mode is different from the first display mode in terms of the number of display rows of the plurality of images displayed,
wherein in the first display mode, the processor is configured to display the reference image at an upper left end of the specific display area, and
wherein in the second display mode, the processor is configured to display the reference image in a leftmost column of the specific display area.

6. The endoscopic image display device according to claim 5,
wherein in the first display mode, if a portion of an image at the leftmost column of the specific display area displayed is outside the specific display area the processor is configured to set an image of the plurality of images at an upper end among images in a column next to the leftmost column as the reference image, and
wherein in the second display mode, the screen is controlled to display the reference image in the leftmost column of the specific display area.

7. The endoscopic image display device according to claim 1,
wherein the processor is configured to receive an image selection instruction issued in response to a user operation of selecting an image to be processed from a plurality of images in the display area, and
wherein the processor is configured to control the screen to scrollably display the plurality of images in the second display mode irrespective of the image that is selected based on the image selection instruction.

8. The endoscopic image display device according to claim 1,
wherein the plurality of images are endoscopic images captured with an endoscope and are stored in an order in which the images are captured.

9. The endoscopic image display device according to claim 1,
wherein the plurality of images are endoscopic images, wherein the screen is a creation screen for a medical document, and
wherein the specific display area is arranged at a portion of the creation screen.

10. The endoscopic image display device according to claim 1,
wherein the plurality of images are a plurality of endoscopic images, and
wherein the plurality of endoscopic images are thumbnail images.

11. A non-transitory computer-readable storage device storing instructions that, upon execution by a processor of an endoscopic image display device, cause the processor to, at least:
control a screen to scrollably display a plurality of images in a first display mode,
wherein in the first display mode, the plurality of images are scrollably displayed in a first arrangement in a specific display area in the screen, and
wherein in the first display mode, a reference image of the plurality of images is displayed at a position in the first arrangement that goes out of the specific display area first upon scroll in a forward direction from a scroll position that is forward of a beginning position of a scrolling range of the first arrangement; and
in response to receiving a display mode switching signal, control the screen to scrollably display the plurality of images in a second display mode,
wherein in the second display mode, the plurality of images are scrollably displayed in a second arrangement in the specific display area in the screen, wherein the second arrangement is different from the first arrangement, and
wherein in the second display mode, the screen is controlled to display the reference image at a position in the second arrangement that goes out of the specific display area first upon scroll in the forward direction.

* * * * *